United States Patent
Allen et al.

(10) Patent No.: US 10,118,044 B2
(45) Date of Patent: Nov. 6, 2018

(54) CONNECTOR BLOCK ASSEMBLY

(71) Applicant: Cardiac Pacemakers, Inc., St. Paul, MN (US)

(72) Inventors: Brian D. Allen, Blaine, MN (US); David A. Chizek, Brooklyn Park, MN (US); James Michael English, Cahir (IE); Mary M. Byron, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/286,663

(22) Filed: Oct. 6, 2016

(65) Prior Publication Data

US 2017/0100596 A1 Apr. 13, 2017

Related U.S. Application Data

(60) Provisional application No. 62/239,643, filed on Oct. 9, 2015.

(51) Int. Cl.
| | |
|---|---|
| *A61N 1/00* | (2006.01) |
| *H01R 33/00* | (2006.01) |
| *A61N 1/375* | (2006.01) |
| *A61N 1/362* | (2006.01) |
| *A61N 1/39* | (2006.01) |
| *H01R 13/502* | (2006.01) |
| *H01R 13/52* | (2006.01) |

(52) U.S. Cl.
CPC ........... *A61N 1/3754* (2013.01); *A61N 1/362* (2013.01); *A61N 1/3752* (2013.01); *A61N 1/3956* (2013.01); *H01R 13/502* (2013.01); *H01R 13/5224* (2013.01)

(58) Field of Classification Search
USPC .......................................... 607/119; 439/651
See application file for complete search history.

(56) References Cited

U.S. PATENT DOCUMENTS

| | | | |
|---|---|---|---|
| 5,679,026 A | * | 10/1997 | Fain ...................... A61N 1/3752 439/651 |
| 6,835,084 B2 | | 12/2004 | Poon et al. |
| 7,110,827 B2 | | 9/2006 | Sage et al. |
| 7,164,951 B2 | | 1/2007 | Ries |
| 7,195,523 B2 | | 3/2007 | Naviaux |
| 7,274,964 B2 | | 9/2007 | Balsells |

(Continued)

FOREIGN PATENT DOCUMENTS

| | | |
|---|---|---|
| EP | 0339877 A2 | 11/1989 |
| WO | WO-2006107994 A2 | 10/2006 |

(Continued)

OTHER PUBLICATIONS

"International Application Serial No. PCT/US2016/055638, International Search Report dated Jan. 20, 2017", 4 pgs.

(Continued)

*Primary Examiner* — Nicole F Johnson
(74) *Attorney, Agent, or Firm* — Schwegman Lundberg & Woessner, P.A.

(57) ABSTRACT

An apparatus including a header mountable to an implantable housing; and an electrically conductive connector block located within the header, wherein the conductive connector block is formed from a substantially non-metallic material.

17 Claims, 4 Drawing Sheets

(56) References Cited

U.S. PATENT DOCUMENTS

| | | |
|---|---|---|
| 7,299,095 B1 | 11/2007 | Barlow et al. |
| 7,722,415 B2 | 5/2010 | Chansrivong |
| 7,914,351 B2 | 3/2011 | Balsells et al. |
| 8,382,532 B2 | 2/2013 | Sjostedt et al. |
| 8,934,974 B2 | 1/2015 | Sage |
| 2003/0163171 A1 | 8/2003 | Kast et al. |
| 2004/0260372 A1 | 12/2004 | Canfield et al. |
| 2005/0107859 A1 | 5/2005 | Daglow et al. |
| 2006/0030893 A1 | 2/2006 | Laske et al. |
| 2006/0224208 A1 | 10/2006 | Naviaux |
| 2007/0161294 A1 | 7/2007 | Brase et al. |
| 2009/0233491 A1 | 9/2009 | Barker et al. |
| 2010/0279558 A1 | 11/2010 | Leon et al. |
| 2013/0046368 A1 | 2/2013 | Storey |

FOREIGN PATENT DOCUMENTS

| | | |
|---|---|---|
| WO | WO-2014004005 A1 | 1/2014 |
| WO | WO-2017062545 A1 | 4/2017 |

OTHER PUBLICATIONS

"International Application Serial No. PCT/US2016/055638, Written Opinion dated Jan. 20, 2017", 5 pgs.

\* cited by examiner

CONNECTOR BLOCK ASSEMBLY

CLAIM OF PRIORITY

This application claims the benefit of priority under 35 U.S.C. § 119(e) of U.S. Provisional Patent Application Ser. No. 62/239,643, filed on Oct. 9, 2015, which is herein incorporated by reference in its entirety.

BACKGROUND

Implantable devices such as pacemakers or defibrillators include a housing and an attached header. The header includes one or more ports to receive a terminal end of an implantable lead. The header includes connector blocks with contacts that electrically communicate with terminal contacts on the lead. The connector block contacts are electrically connected to feedthroughs which contact electronics within the housing.

Most commercially available implantable pulse generator devices utilize a connector block having a metallic housing to support coil contacts for the purposes of transferring energy from the pulse generator to a lead or an electrode. U.S. Pat. No. 7,110,827 discusses header contacts for an implantable device.

OVERVIEW

Example 1 can include subject matter that can include an apparatus including a header mountable to an implantable housing; and an electrically conductive connector block located within the header, wherein the conductive connector block is formed from a substantially non-metallic material.

In Example 2, the subject matter of claim 1 can optionally include the conductive connector block including a conductive moldable material, a conductive printable material, a conductive extrudable material, or a conductive e-spun material.

In Example 3, the subject matter of example 2 can optionally include the material including a conductive polymer, silicone, or composite material.

In Example 4, the subject matter of any of examples 1-3 can optionally include the conductive connector block being formed of a non-conductive material with a conductive coating.

In Example 5, the subject matter of any of examples 1-4 can optionally include an electrical contact within the connector block for the purposes of transferring energy from the implantable housing to a lead or an electrode.

In Example 6, the subject matter of example 5 can optionally include the connector block completely surrounding the electrical contact.

In Example 7, the subject matter of example 5 can optionally include the connector block not completely enclosing the electrical contact In Example 8, the subject matter of any of examples 1-7 can optionally include the conductive connector block directly interfacing with a lead or electrode.

In Example 9, the subject matter of any of examples 1-8 can optionally include the connector block being formed of two or more parts.

In Example 10, the subject matter of any of examples 1-9 can optionally include the connector block being connected to exterior elements through staking, use of a mechanical interlock, direct contact, interference fit, bonding, or incorporating the electrical contact into the molded or print component.

Example 11 can include subject matter that can include an apparatus including an implantable housing holding pulse generator electronics; a header mounted to the implantable housing; and a conductive connector block located within the header and configured to receive a lead, wherein the conductive connector block is formed from a substantially non-metallic material, the conductive connector block electrically attached to a feedthrough which extends between the header and the implantable housing.

In Example 12, the subject matter of example 11 can optionally include the conductive connector block including a conductive moldable material, a conductive printable material, a conductive extrudable material, or a conductive e-spun material.

In Example 13, the subject matter of example 12 can optionally include the material including a conductive polymer, silicone, or composite material.

In Example 14, the subject matter of any of examples 11-13 can optionally include the conductive connector block being formed of a non-conductive material with a conductive coating.

Example 15 can include subject matter that can include a method including placing an electrically conductive connector block into a header of an implantable device wherein the conductive connector block is formed from a non-metallic material; and connecting the electrically conductive connector block to a feedthrough.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
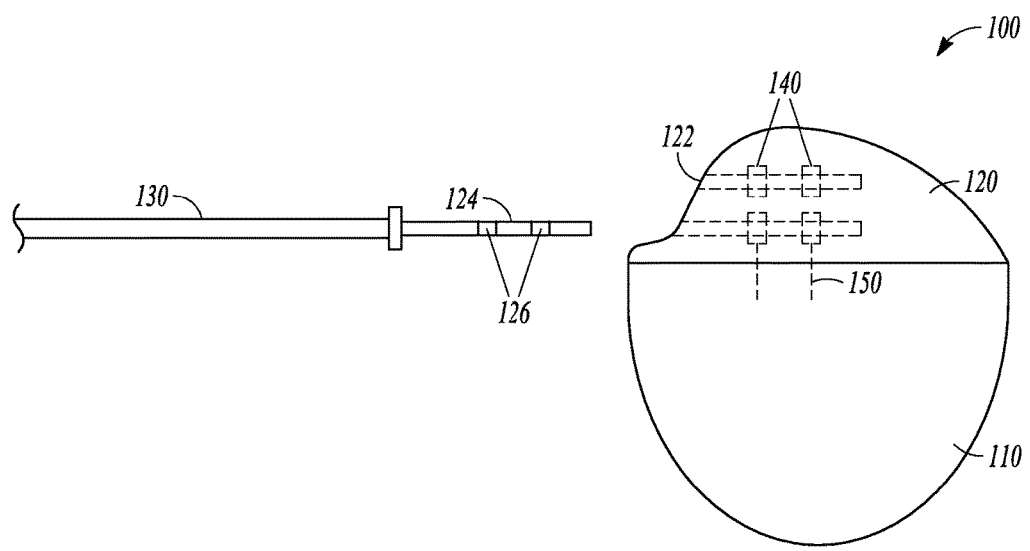
FIG. 1 shows an implantable medical device in accordance with one example.

FIG. 1 shows an implantable medical device 100 in accordance with one example. The implantable medical device 100 includes a metallic housing 110 and an attached header 120. The header 120 includes one or more ports 122 to receive a terminal pin 124 of an implantable lead 130. The lead 130 is configured to deliver pacing pulses, defibrillation shock energy, or cardioversion therapy to a heart, for example. The implantable medical device 100 can be implanted in a surgically-formed pocket in a patient's chest or other desired location.

The implantable medical device 100 generally includes electronic components to perform signal analysis, processing, and control. The implantable medical device 100 can include a power supply such as a battery, a capacitor, and other components housed within housing 110. The implantable medical device 100 can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia via one or more electrodes of the lead 130.

This device 100 includes one or more connector blocks 140 that connect to feedthroughs 150 to electrically communicate between the header 120 and the electronics within housing 100. Terminal contacts 126 on terminal 124 contact the connector blocks 140 to electrically communicate with electrodes on the lead 130.

As will be explained further below, connector blocks 140 can be made from, fully or partially, a non-metallic or a substantially non-metallic material such as a conductive polymer, silicone, composite, or other molded material (coated or uncoated) to replace the previous metallic connector blocks. By eliminating the metallic connector block the overall size of the coil contact supporting structure can be decreased allowing for the header volume of the pulse generator to be decreased. In some embodiments the connector blocks include no metallic material and can be conductive polymers/silicones/plastics or composite materials.

In some embodiments, the substantially non-metallic connector blocks 140 can be made from a polymer, silicone, or molded/printed material that may contain small amounts of metals or other conductive materials to make them conductive or improve conductivity. Thus, while the base material may not be metallic, there may be a low percentage of metallic material present. For example, some conductive silicones can contain bits of titanium or other metals to make them conductive. Most applicable conductive materials available today have little metal, and in one or more examples discussed herein, the substantially metallic material is material with a non-metallic base material and less than 10% metal. In one or more of the examples herein, the substantially metallic material is material with a non-metallic base material and having less than 50% metal. In other examples, the metallic content can be any percentage in a range from 0% (e.g. non-metallic) to less than 50% metallic.

By eliminating a fully metallic connector block, it also provides an opportunity for a physician to monitor the location of the lead or electrode while it is implanted using fluoroscopy. The absence of a conventional metallic connector block can also positively impact the performance of the medical device during MRI scans, and improve the RF performance over certain material alternatives.

Figure 2:
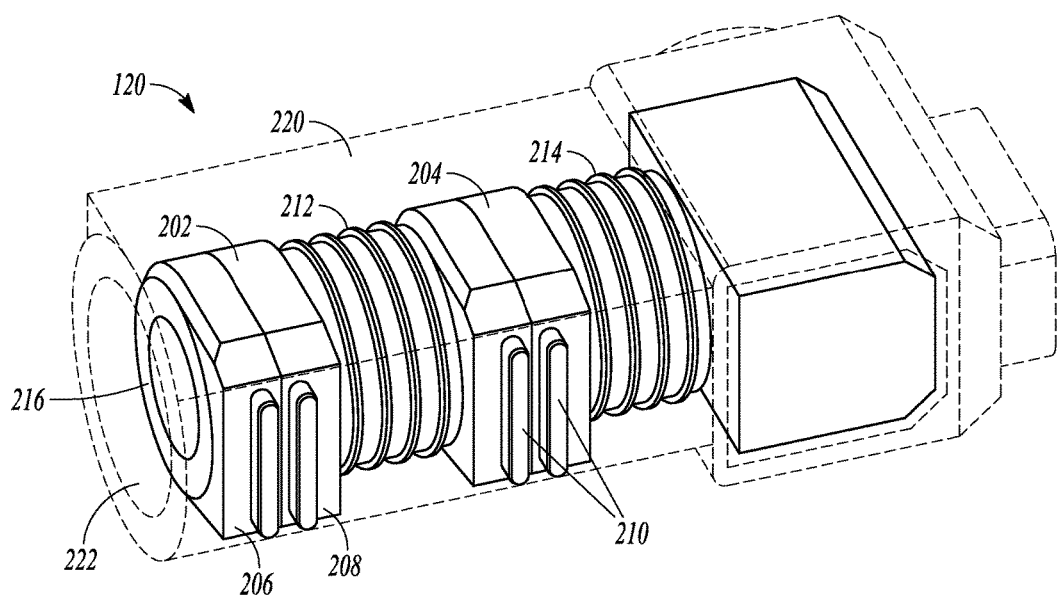
FIG. 2 shows a perspective view of connector block within a header of an implantable medical device, in accordance with one example.

FIG. 2 shows a perspective view of connector blocks 202, 204 within a header core 220 of a header of an implantable medical device, in accordance with one example. The connector blocks 202, 204 can be an electrically conductive connector blocks located within the header. The conductive connector blocks 202, 204 can be formed from moldable or printable substantially non-metallic material.

The header core 220 can include can include one or bores 222 formed in the header core 220 and aligned with bores 122 (FIG. 1) to receive a terminal pin of a lead. The header core 220 can include one or more connector block cavities shaped and dimensioned to each receive a respective connector block 202, 204. Insulating seals 212 and 214 are placed adjacent the connector blocks 202, 204. The connector blocks 202, 204 can be connected to feedthroughs that extend from the header into a housing of an implantable device, as discussed for FIG. 1. Thus, the connector blocks 202, 204 can receive a lead terminal pin and electrically couple the lead terminal pin to electronics within the housing via the feedthrough.

In this example, each connector block 202, 204 is formed from two (or more) separately molded or 3D-printed connector halves 206, 208. The halves can also be formed from extruded or e-spun materials. The two halves 206, 208 can be separately formed with internal cavities such that an electrical contact such as a spring coil contact 216 can be placed between the two halves. The coil contact 216 within the connector block acts to transfer energy between the implantable device and a lead or an electrode. In this example, each connector block 202, 204 can completely surround the coil contact 216. In other examples, as will be discussed below, the connector block only partially encloses the coil contact. In one example, the connector blocks 202, 204 can be constructed as a unitary structure using an additive manufacturing process, such as printing.

In another example, coil contact 216 is omitted, and the connector blocks 202, 204 are formed with an internal shape to directly interface with the terminal of the lead as the electrical contact themselves. For example, by using silicon or another material with a lower modulus, the material of the connector blocks 202, 204 can act as a spring by itself, without the need for a separate electrical contact.

In some embodiments, the electrical contact, such as a spring or coil contact can be manufactured or printed independently, or in conjunction with the housing.

In this example, each connector block 202, 204 can include one or more protrusions 210 extending from an outer surface of the connector block 202, 204. The protrusions 210 can be directly connected to a feedthrough or connected to a conductor that leads to a feedthrough. In one example, a connection to an external component can be made by crimping the connector between the two protrusions 210 on each connector block 202, 204. In some examples, the connector blocks 202, 204 can be connected to an exterior electrical contact (such as a feedthrough or conductor) through staking, use of a mechanical interlock, direct contact, interference fit, bonding, or incorporating the electrical contact into the molded or printed component.

To form the connector blocks 202, 204 the conductive connector blocks 202, 204 can include a conductive moldable or 3D-printable material. For example, some materials can include a conductive polymer, a conductive silicone, or a composite conductive material. In another example, the connector blocks 202, 204 can be formed of a moldable or printable non-conductive material and a conductive coating can be applied to the exterior surfaces of the connector block. In some examples, the connector blocks can be formed of conductive extrudable, or printable materials, or materials constructed wholly or partially with an e-spin material.

Figure 3:
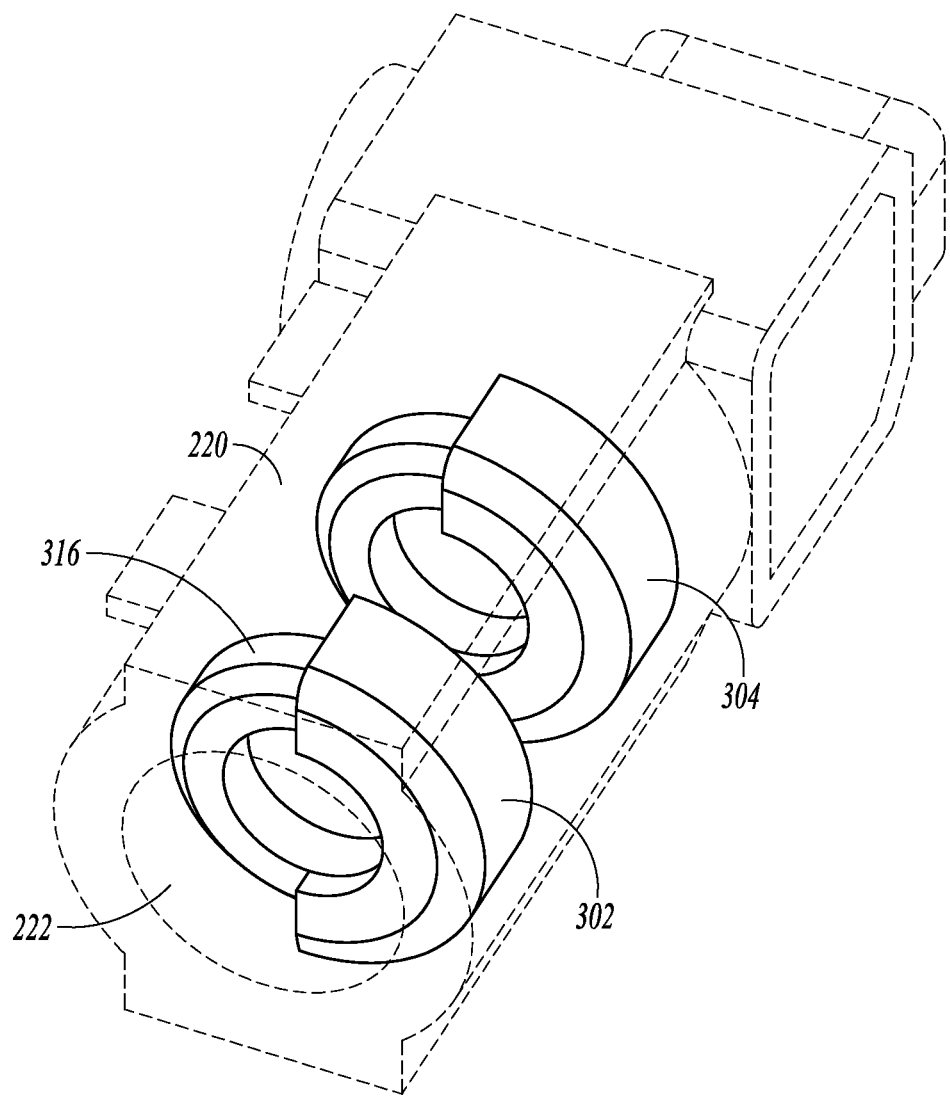
FIG. 3 shows a perspective view of a connector block in accordance with one example.

FIG. 3 shows a perspective view of connector blocks 302, 304 in accordance with one example. As with connector blocks 202, 204 discussed above, the connector blocks 302, 304 can be an electrically conductive connector blocks located within the bore 222 of the header. The conductive connector block 302, 304 can be formed from moldable or printable substantially non-metallic material.

In this example, the connector blocks 302, 304 do not completely enclose a coil contact 316, with the coil contact 316 only partially surrounded by the connector block 302, 304 with the header core providing support to the coil contact 316. The coil contact 316 can be partially molded into the connector block 302, 304.

In some examples, the connector blocks 302, 304 can be connected to an exterior electrical contact (such as a feedthrough or conductor) through staking, use of a mechanical interlock, direct contact, interference fit, bonding, or incorporating the electrical contact into the molded or printed component.

As with the example discussed above, the conductive connector blocks 302, 304 can include a conductive moldable or 3D-printable material. For example, some materials can include a conductive polymer, a conductive silicone, or a composite conductive material. In another example, the connector block 302, 304 can be formed of a moldable or printable non-conductive material and a conductive coating can be applied to the exterior surfaces of the connector block.

Figure 4:
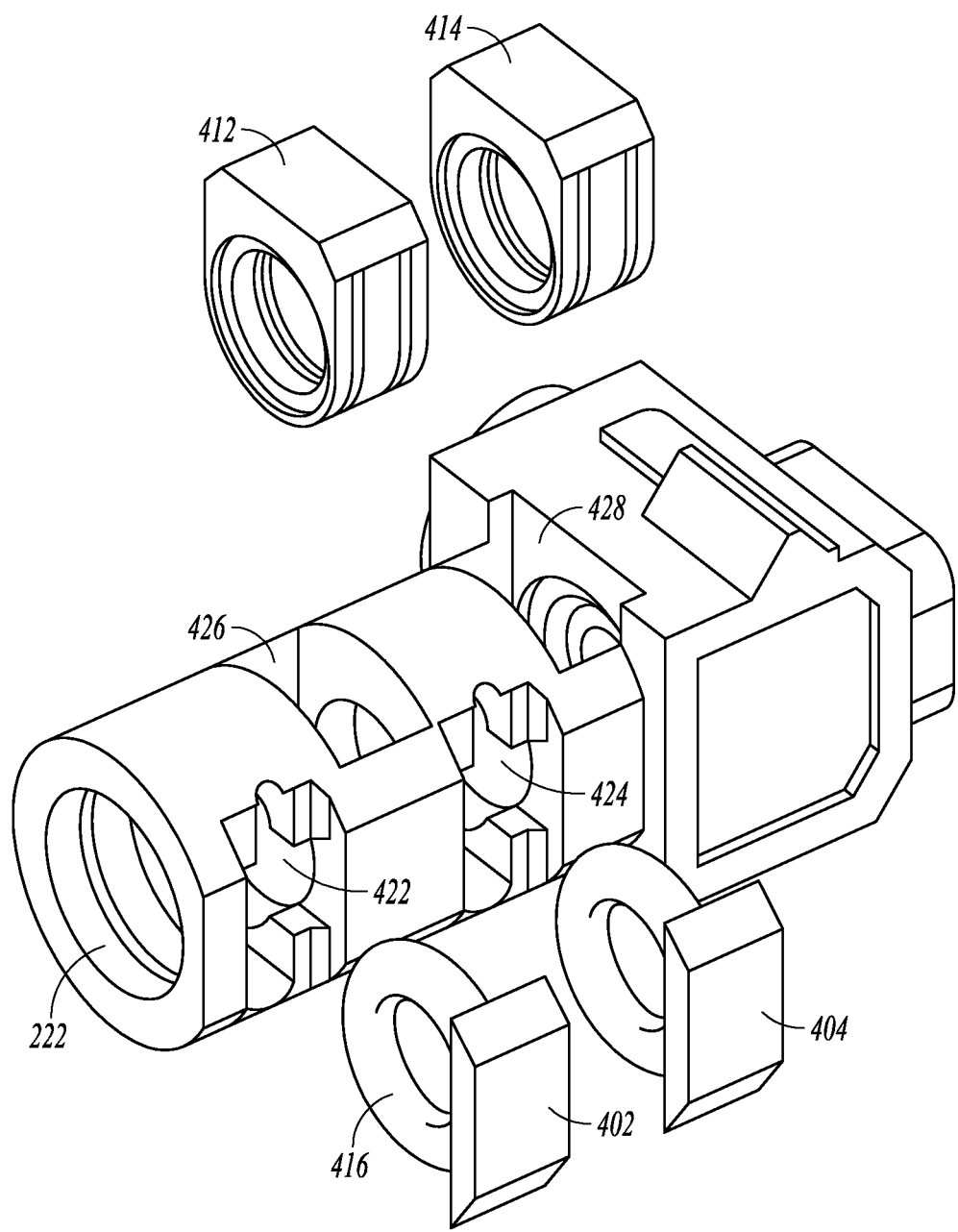
FIG. 4 shows a perspective view of a connector block in accordance with one example.
Figure 5:
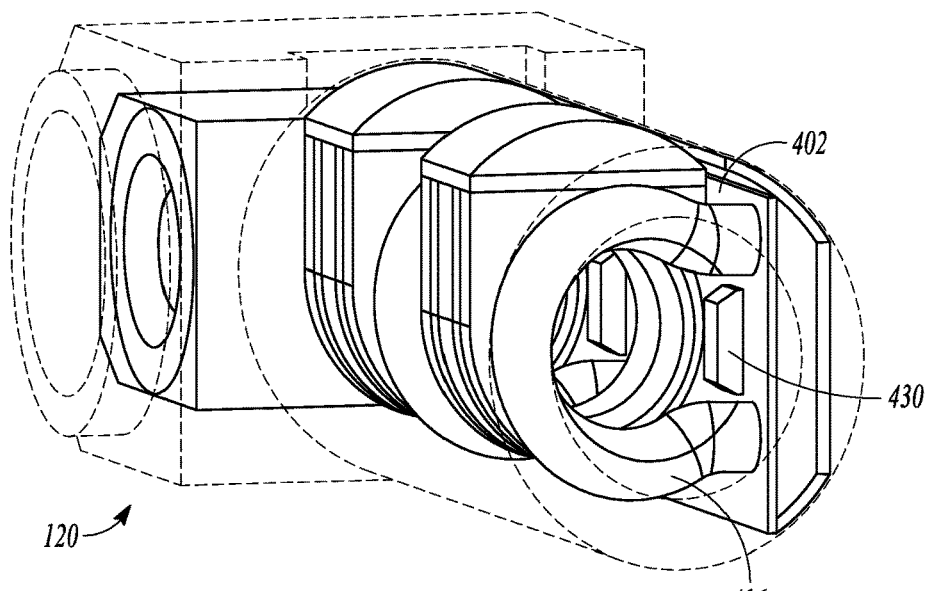
FIG. 5 shows another perspective view of the connector block of FIG. 4.

FIG. 4 shows a perspective view of connector blocks 402, 404 in accordance with one example. FIG. 5 shows another perspective view of the connector blocks 402, 404. As with the connector blocks discussed above, the connector blocks 402, 404 can be an electrically conductive connector blocks located within the bore 222 of the header. The conductive connector blocks 402, 404 can be formed from moldable or printable substantially non-metallic material.

In this example, the header can include cavities 422, 424 to receive respective connector block 402, 404. Cavities 426 and 428 can be provided to receive insulating seals 412 and 414 that can be placed adjacent the connector blocks 402, 404

In this example, the connector blocks 402, 404 do not completely enclose a coil contact 416, with the coil contact 416 only partially coupled by the connector block 402, 404.

Here, connector blocks 402, 404 are planar members with the coil contact 416 either located within or molded within the connector block 402, 404. In other examples the outer or inner surfaces of connector blocks 402, 404 can be curved or have any shape or contours compatible with the header and for ease of connection to the feedthrough. An outer surface of each connector block 402 and 404 is exposed to be connected to a feedthrough or conductor. An inner surface of the connector block can optionally include a protrusion 430 located where the contact 416 is within the connector block 402. Other embodiments of conductor block 402, with different electrical contacts, which will be discussed below, do not have to have a protrusion. Protrusion 430 provides structure to support the side load exerted by the lead when inserted. Here, spring coil contact 416 is not rounded and includes two legs or sections entering the connector block 402, with protrusion 430 located there between.

In some examples, the connector blocks 402, 404 can be connected to an exterior electrical contact (such as a feedthrough or conductor) through staking, use of a mechanical interlock, direct contact, interference fit, bonding, or incorporating the electrical contact into the molded or printed component.

As with the example discussed above, the conductive connector blocks 402, 404 can include a conductive moldable or 3D-printable material, or an extrudable or e-spun material. For example, some materials can include a conductive polymer, a conductive silicone, or a composite conductive material. In another example, the connector block 402, 404 can be formed of a moldable or printable non-conductive material and a conductive coating can be applied to the exterior surfaces of the connector block.

In other examples, the electrical contact can include the formed composite material acting as a spring with solid metallic members to contact the lead. The metallic or composite members may number one or more, may not have consistent cross-section throughout its length, and may not be straight.

Figure 6:
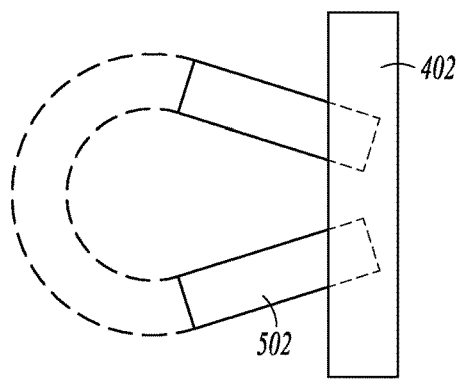
FIG. 6 shows a connector block, in accordance with one embodiment.

For example, FIG. 6 shows the connector block 402, in accordance with one embodiment. Here the electrical contact 502 includes a pair of legs extending from the surface of the connector block 402. The electrical contact 502 can be springs or formed metal. The dashes of FIG. 6 show how the contact 502 has a geometric similarity to contact 416 of FIG. 6.

Figure 7:
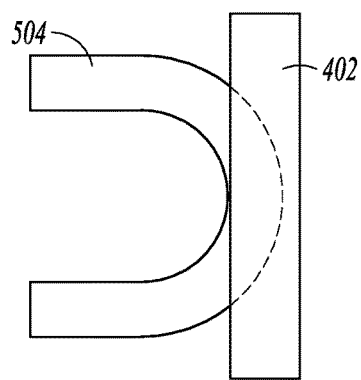
FIG. 7 shows a connector block, in accordance with one embodiment.

FIG. 7 shows the connector block 402, in accordance with one embodiment. Here the electrical contacts include a semi-circular shape with an open end and having a portion molded within the conductor block 402.

Figure 8:
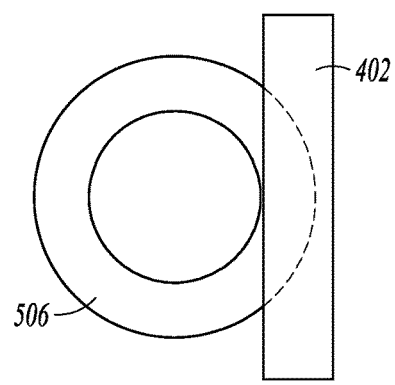
FIG. 8 shows a connector block, in accordance with one embodiment.

FIG. 8 shows a connector block 402, in accordance with one embodiment. Here the electrical contact 506 is circular and is at least partially molded with the connector block 402.

As noted above, most implantable pulse generator devices utilize metallic connector blocks to support coil contacts for the purposes of transferring energy from the pulse generator to a lead or an electrode.

In any of the examples discussed above, the connector block or assembled components making up the connector block are molded (for example, injection molded) or 3D-printed, or extruded or e-spun and interface with, or acts as an electrical contact to support a lead or electrode. The connector block can be made of one or more molded or printed components and materials. The material can be conductive, or contain conductive material(s), or be a non-conductive material with a conductive coating, such as a titanium coating.

The present connector blocks can replace all the metallic contacts used in pacemaker, defibrillator, neuromodulation and CRT devices. The connector block discussed above can be used in any similarly configure devices in the future. The connector blocks can allow for the size of the header assembly to be decreased. The connector blocks can give physicians an improved ability to determine the state of lead insertion within the header under fluoroscopy. In another example, the connector blocks can improve performance in MRI and RF telemetry performance when compared to some alternative materials.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising:
a header mountable to an implantable housing; and
an electrically conductive connector block located within the header, wherein the conductive connector block is formed from a substantially non-metallic material, wherein the conductive connector block is formed of a non-conductive material with a conductive coating.

2. The apparatus of claim 1, including an electrical contact within the connector block for the purposes of transferring energy from the implantable housing to a lead or an electrode.

3. The apparatus of claim 2, wherein the connector block completely surrounds the electrical contact.

4. The apparatus of claim 2, wherein the connector block does not completely enclose the electrical contact.

5. The apparatus of claim 1, wherein the conductive connector block directly interfaces with a lead or electrode.

6. The apparatus of claim 1, wherein the connector block is formed of two or more parts.

7. The apparatus of claim 1, wherein the connector block is connected to exterior elements through staking, use of a mechanical interlock, direct contact, interference fit, bonding, or incorporating the electrical contact into the molded or print component.

8. An apparatus comprising:
an implantable housing holding pulse generator electronics;
a header mounted to the implantable housing; and
a conductive connector block located completely within the header and configured to receive a lead, wherein the conductive connector block is formed from a substantially non-metallic material with the entire outer surface of the conductor block being electrically conductive, the conductive connector block electrically attached to a feedthrough which extends between the header and the implantable housing.

9. The apparatus of claim 8, wherein the conductive connector block includes a conductive moldable material, a conductive printable material, a conductive extrudable material, or a conductive e-spun material.

10. The apparatus of claim 9, wherein the material includes a conductive polymer, silicone, or composite material.

11. The apparatus of claim 8, wherein the conductive connector block is formed of a non-conductive material with a conductive coating.

12. The apparatus of claim 8, including an electrical contact contacting the connector block for the purposes of transferring energy from the implantable to a lead or an electrode.

13. The apparatus of claim 8, wherein the conductive connector block directly interfaces with a lead or electrode.

14. The apparatus of claim 8, wherein the connector block is connected to exterior elements through staking, use of a mechanical interlock, direct contact, interference fit, bonding, or incorporating the electrical contact into the molded or print component.

15. A method comprising:
placing an electrically conductive connector block into a header of an implantable device such that the connector block is completely within the header, wherein the conductive connector block is formed from a substantially non-metallic material with the entire outer surface of the conductor block being electrically conductive; and
connecting the electrically conductive connector block to a feedthrough.

16. The method of claim 15, a conductive moldable material, a conductive printable material, a conductive extrudable material, or a conductive e-spun material.

17. The apparatus of claim 15, wherein the conductive connector block is formed of a non-conductive material with a conductive coating.

* * * * *